US011155886B2

(12) United States Patent
Dugenny et al.

(10) Patent No.: US 11,155,886 B2
(45) Date of Patent: Oct. 26, 2021

(54) COMPOSITIONS AND METHODS FOR DETECTION OF ZIKA VIRUS

(71) Applicant: Roche Molecular Systems, Inc., Pleasanton, CA (US)

(72) Inventors: Slav Dugenny, San Leandro, CA (US); Ellen H Fiss, Albany, CA (US); Jeffery Fong, Lafayette, CA (US); Marintha Heil, Danville, CA (US); Eugene Spier, Los Altos, CA (US); Jingtao Sun, San Ramon, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

(21) Appl. No.: 16/840,610

(22) Filed: Apr. 6, 2020

(65) Prior Publication Data

US 2020/0232051 A1    Jul. 23, 2020

Related U.S. Application Data

(62) Division of application No. 15/456,071, filed on Mar. 10, 2017, now Pat. No. 10,655,190.

(60) Provisional application No. 62/327,688, filed on Apr. 26, 2016, provisional application No. 62/306,803, filed on Mar. 11, 2016.

(51) Int. Cl.
  *C12Q 1/70*     (2006.01)
  *C12Q 1/6818*   (2018.01)

(52) U.S. Cl.
  CPC .......... *C12Q 1/701* (2013.01); *C12Q 1/6818* (2013.01); *C12Q 2600/158* (2013.01); *Y02A 50/30* (2018.01)

(58) Field of Classification Search
  CPC ...... Y02A 50/30; Y02A 50/51; C12Q 1/6818; C12Q 1/701; C12Q 2600/158
  See application file for complete search history.

(56) References Cited

U.S. PATENT DOCUMENTS

2014/0113279 A1*  4/2014  Babiel .................. C12Q 1/707
                                                    435/5

OTHER PUBLICATIONS

Faye et al., "One-step RT-PCR for detection of Zika virus," Journal of Clinical Virology, vol. 43, pp. 96-101. (Year: 2008).*
Lanciotti et al., "Genetic and Serologic Properties of Zika Virus Associated with an Epidemic, Yap State Micronesia, 2007", Emerging Infectious Diseases, August, vol. 14, No. 8, pp. 1232-1239. (Year: 2008).*
Gen Bank Accession No. MK049248 [retrieved on-line, Nov. 2018, retrieval date, Apr. 11, 2019, retrieved from: https://www.ncbi.nlm.nih.gov/nuccore/MK049248.1?report=GenBank#sequence_MK049248.1] (Year: 2018).*

* cited by examiner

*Primary Examiner* — Young J Kim
(74) *Attorney, Agent, or Firm* — Eric Grant Lee

(57) ABSTRACT

Methods for the rapid detection of the presence or absence of Zika virus in a biological or non-biological sample are described. The methods can include performing an amplifying step, a hybridizing step, and a detecting step. Furthermore, primers and probes targeting Zika virus and kits are provided that are designed for the detection of Zika virus.

9 Claims, 4 Drawing Sheets
Specification includes a Sequence Listing.

FIGURE 4

COMPOSITIONS AND METHODS FOR DETECTION OF ZIKA VIRUS

CROSS REFERENCE TO RELATED APPLICATIONS

This application is a divisional patent application of U.S. patent application Ser. No. 15/456,071, filed Mar. 10, 2017, which claims the benefit of priority of U.S. Provisional Patent Application Nos. 62/306,803, filed Mar. 11, 2016, and 62/327,688, filed Apr. 26, 2016, which are incorporated herein by reference in their entirety.

FIELD OF THE INVENTION

The present disclosure relates to the field of viral diagnostics, and more particularly to detection of Zika virus.

BACKGROUND OF THE INVENTION

Zika virus, a member of the family Flaviviridae and the genus *Flavivirus*, is a virus that is transmitted by Aedes mosquitoes, which include *A. aegypti* and *A. albopictus*. Zika virus is related to dengue virus, yellow fever virus, Japanese encephalitis virus (JEV), and West Nile virus (WNV). Infection by the Zika virus is known as Zika fever, which in humans, may cause fever, rash, and malaise. Zika virus infection is linked with neurologic conditions in adults, including the Guillain-Barré syndrome. Additionally, as of early 2016, Zika virus infection in pregnant women has been linked with miscarriage and/or microcephaly. To date, there are no known effective drug treatments for or vaccines against Zika virus infection.

In 2013-2014, there were epidemic outbreaks of Zika virus in Oceania. In May 2015, the first confirmed case of Zika virus infection was identified in Brazil. Since May 2015, there have been an estimated 440,000 to 1,300,000 people infected in Brazil. The recent outbreaks in Brazil have been linked with the high number of claims of microencephaly. As of early 2016 a widespread outbreak of Zika virus was ongoing, primarily in the Americas, originating from Brazil and spreading to other countries in South America, Central America, Mexico, and the Caribbean.

Serological tests (enzyme-linked immunosorbent assay (ELISA) or immunofluorescence) for Zika virus have been developed. However, cross-reactivity with other flaviviruses, including dengue or yellow fever, limits the utility of an IgM antibody diagnostic test. Moreover, antibodies may not be present in the early phase of the infection, which further reduces the utility and suitability of a serologic test for acute infection. Thus, there is a need in the art for a quick, reliable, specific, and sensitive method to detect Zika virus.

SUMMARY OF THE INVENTION

Certain embodiments in the present disclosure relate to methods for the rapid detection of the presence or absence of Zika virus in a biological or non-biological sample, for example, multiplex detection of Zika virus by quantitative real-time reverse-transcriptase polymerase chain reaction (PCR) in a single test tube. Embodiments include methods of detection of Zika virus comprising performing at least one cycling step, which may include an amplifying step and a hybridizing step. Furthermore, embodiments include primers, probes, and kits that are designed for the detection of Zika virus in a single tube. The detection methods are designed to target various regions of the Zika virus genome. For example, the methods are designed to target the region of the genome that encodes the envelope (E) region, and/or target non-structural (NS) regions, such as NS3, NS4B, and NS5.

In one embodiment, a method for detecting Zika virus in a sample is provided, comprising performing an amplifying step including contacting the sample with a set of primers to produce an amplification product if Zika virus is present in the sample; performing a hybridizing step including contacting the amplification product with one or more detectable probes; and detecting the presence or absence of the amplified product, wherein the presence of the amplified product is indicative of the presence of Zika virus in the sample and wherein the absence of the amplified product is indicative of the absence of Zika virus in the sample; wherein the set of primer comprises or consists of a sequence selected from the group consisting of SEQ ID NOs:1, 2, 3, 4, 5, 6, 7, and 8, or a complement thereof; and wherein the detectable probe comprises or consists of a sequence selected from the group consisting of SEQ ID NOs:9, 10, 11, and 12, or a complement thereof.

In one embodiment, the primer set for amplification of the Zika virus target includes a first primer comprising a first oligonucleotide sequence selected from the group consisting of SEQ ID NOs:1, 2, 3, and 4, or a complement thereof, and a second primer comprising a second oligonucleotide sequence selected from the group consisting of SEQ ID NOs:5, 6, 7, and 8, or a complement thereof, and the detectable probe for detection of the amplification product includes the nucleic acid sequences of SEQ ID NOs:9, 10, 11, and 12, or a complement thereof.

Other embodiments provide an oligonucleotide comprising or consisting of a sequence of nucleotides selected from SEQ ID NOs:1-12, or a complement thereof, which oligonucleotide has 100 or fewer nucleotides. In another embodiment, the present disclosure provides an oligonucleotide that includes a nucleic acid having at least 70% sequence identity (e.g., at least 75%, 80%, 85%, 90% or 95%, etc.) to one of SEQ ID NOs:1-12, or a complement thereof, which oligonucleotide has 100 or fewer nucleotides. Generally, these oligonucleotides may be primer nucleic acids, probe nucleic acids, or the like in these embodiments. In certain of these embodiments, the oligonucleotides have 40 or fewer nucleotides (e.g., 35 or fewer nucleotides, 30 or fewer nucleotides, 25 or fewer nucleotides, 20 or fewer nucleotides, 15 or fewer nucleotides, etc.) In some embodiments, the oligonucleotides comprise at least one modified nucleotide, e.g., to alter nucleic acid hybridization stability relative to unmodified nucleotides. Optionally, the oligonucleotides comprise at least one label and optionally at least one quencher moiety. In some embodiments, the oligonucleotides include at least one conservatively modified variation.

"Conservatively modified variations" or, simply, "conservative variations" of a particular nucleic acid sequence refers to those nucleic acids, which encode identical or essentially identical amino acid sequences, or, where the nucleic acid does not encode an amino acid sequence, to essentially identical sequences. One of skill in the art will recognize that individual substitutions, deletions or additions which alter, add or delete a single nucleotide or a small percentage of nucleotides (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid.

In one aspect, amplification can employ a polymerase enzyme having 5' to 3' nuclease activity. Thus, the donor fluorescent moiety and the acceptor moiety, e.g., a quencher, may be within no more than 5 to 20 nucleotides (e.g., within 8 or 10 nucleotides) of each other along the length of the probe. In another aspect, the probe includes a nucleic acid sequence that permits secondary structure formation. Such secondary structure formation may result in spatial proximity between the first and second fluorescent moiety. According to this method, the second fluorescent moiety on the probe can be a quencher.

In one aspect, the specific Zika virus probes may be labeled with a fluorescent dye which acts as a reporter. The probe may also have a second dye which acts as a quencher. The reporter dye is measured at a defined wavelength, thus permitting detection and discrimination of the amplified Zika virus target. The fluorescent signal of the intact probes is suppressed by the quencher dye. During the PCR amplification step, hybridization of the probes to the specific single-stranded DNA template results in cleavage by the 5' to 3' nuclease activity of the DNA polymerase resulting in separation of the reporter and quencher dyes and the generation of a fluorescent signal. With each PCR cycle, increasing amounts of cleaved probes are generated and the cumulative signal of the reporter dye is concomitantly increased. Optionally, one or more additional probes (e.g., such as an internal reference control or other targeted probe (e.g., other viral nucleic acids) may also be labeled with a reporter fluorescent dye, unique and distinct from the fluorescent dye label associated with the Zika virus probe. In such case, because the specific reporter dyes are measured at defined wavelengths, simultaneous detection and discrimination of the amplified Zika target and the one or more additional probes is possible.

The present disclosure also provides for methods of detecting the presence or absence of Zika virus, or Zika virus nucleic acid, in a biological sample from an individual. These methods can be employed to detect the presence or absence of Zika virus or Zika virus nucleic acid in plasma, for use in blood screening and diagnostic testing. Additionally, the same test may be used by someone experienced in the art to assess urine and other sample types to detect Zika virus or Zika virus nucleic acid. Such methods generally include performing at least one cycling step, which includes an amplifying step and a dye-binding step. Typically, the amplifying step includes contacting the sample with a plurality of pairs of oligonucleotide primers to produce one or more amplification products if a nucleic acid molecule is present in the sample, and the dye-binding step includes contacting the amplification product with a double-stranded DNA binding dye. Such methods also include detecting the presence or absence of binding of the double-stranded DNA binding dye into the amplification product, wherein the presence of binding is indicative of the presence of Zika virus or Zika virus nucleic acid in the sample, and wherein the absence of binding is indicative of the absence of Zika virus or Zika virus nucleic acid in the sample. A representative double-stranded DNA binding dye is ethidium bromide. Other nucleic acid-binding dyes include DAPI, Hoechst dyes, PicoGreen®, RiboGreen®, OliGreen®, and cyanine dyes such as YO-YO® and SYBR® Green. In addition, such methods also can include determining the melting temperature between the amplification product and the double-stranded DNA binding dye, wherein the melting temperature confirms the presence or absence of Zika virus or Zika virus nucleic acid.

In a further embodiment, a kit for detecting one or more nucleic acids of Zika virus is provided. The kit can include one or more sets of primers specific for amplification of the gene target; and one or more detectable oligonucleotide probes specific for detection of the amplification products.

In one aspect, the kit can include probes already labeled with donor and corresponding acceptor moieties, e.g., another fluorescent moiety or a dark quencher, or can include fluorophoric moieties for labeling the probes. The kit can also include nucleoside triphosphates, nucleic acid polymerase, and buffers necessary for the function of the nucleic acid polymerase. The kit can also include a package insert and instructions for using the primers, probes, and fluorophoric moieties to detect the presence or absence of Zika virus nucleic acid in a sample.

Unless otherwise defined, all technical and scientific terms used herein have the same meaning as commonly understood by one of ordinary skill in the art to which this invention belongs. Although methods and materials similar or equivalent to those described herein can be used in the practice or testing of the present subject matter, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

BRIEF DESCRIPTION OF THE FIGURES

FIG. 4 shows PCR growth curves of experiments showing that the primers and probes detect Zika virus from a biological sample, e.g., plasma.

DETAILED DESCRIPTION OF THE INVENTION

Figure 1:
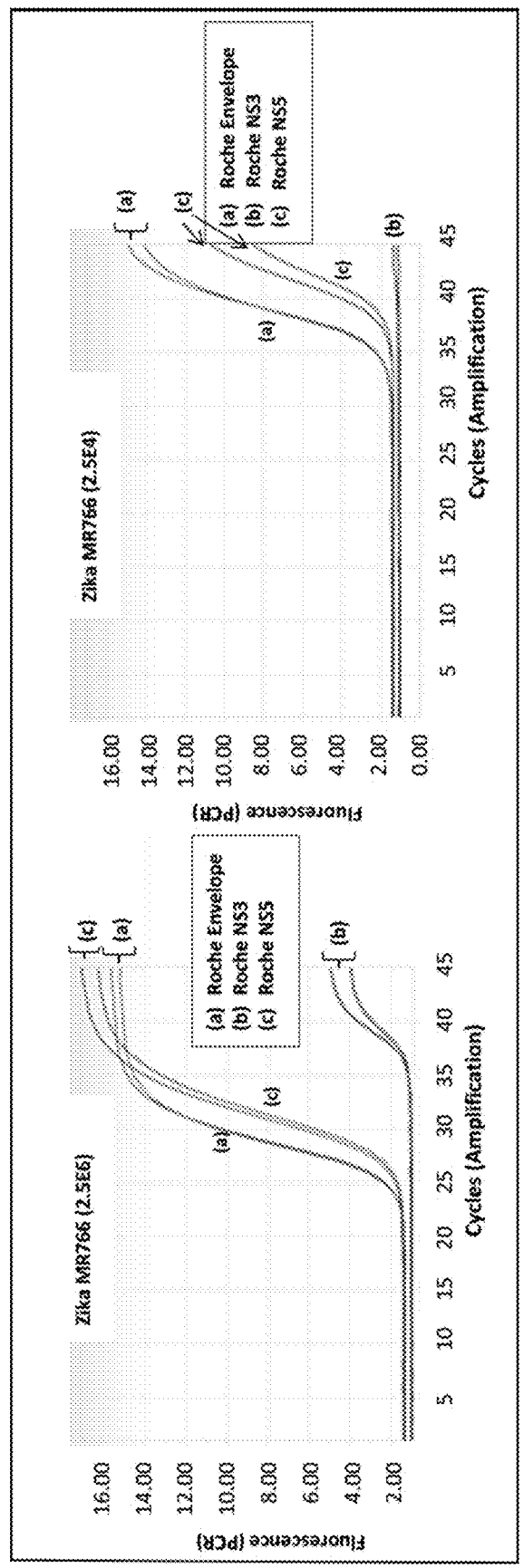
FIG. 1 shows PCR growth curves of experiments showing that the primers and probes specific for the E, NS3, and NS5 regions of the Zika virus genome detect Zika virus.

Diagnosis of Zika virus infection by nucleic acid amplification provides a method for rapidly, accurately, reliably, specifically, and sensitively detecting the viral infection. A quantitative real-time reverse-transcriptase PCR assay for detecting Zika virus in a non-biological or biological sample is described herein. Primers and probes for detecting Zika virus are provided, as are articles of manufacture or kits containing such primers and probes. The increased specificity and sensitivity of real-time PCR for detection of Zika virus compared to other methods, as well as the improved features of real-time PCR including sample containment and real-time detection of the amplified product, make feasible the implementation of this technology for routine diagnosis of Zika virus infections in the clinical laboratory. Additionally, this technology may be employed for blood screening as well as for prognosis. This Zika virus detection assay may also be multiplexed with other assays for the detection of other nucleic acids, e.g., dengue virus, chikungunya virus, and West Nile virus, in parallel.

The Zika virus genome is a positive sense single-stranded RNA molecule 10,794 bases long with two non-coding regions known as the 5'NCR and the 3' NCR. The open reading frame of the Zika virus reads 5'-C-prM-E-NS1-NS2A-NS2B-NS3-NS4A-NS4B-NS5-3'. It encodes for a polypeptide that is subsequently cleaved into capsid (C), precursor membrane (prM), envelope (E), and non-structural proteins (NS). The envelope comprises most of the virion surface and is involved with aspects of replication.

The present disclosure includes oligonucleotide primers and fluorescent labeled hydrolysis probes that hybridize to the Zika virus genome (e.g., aa region of the genome that encodes the envelope (E) region, and/or target non-structural (NS) regions, such as NS3, NS4B, and NS5), in order to specifically identify Zika virus using, e.g., TaqMan® amplification and detection technology. The oligonucleotides specifically hybridize to the envelope (E) region, and/or target non-structural (NS) regions, such as NS3, NS4B, and NS5. Having oligonucleotides that hybridize to multiple locations in the genome is advantageous for improved sensitivity compared to targeting a single copy genetic locus.

The disclosed methods may include performing at least one cycling step that includes amplifying one or more portions of the nucleic acid molecule gene target from a sample using one or more pairs of primers. "Zika virus primer(s)" as used herein refer to oligonucleotide primers that specifically anneal to nucleic acid sequences found in the Zika virus genome, and initiate DNA synthesis therefrom under appropriate conditions producing the respective amplification products. Examples of nucleic acid sequences found in the Zika virus genome, include nucleic acids within the envelope (E) region, and/or target non-structural (NS) regions, such as NS3, NS4B, and NS5. Each of the discussed Zika virus primers anneals to a target within the envelope (E) region, and/or target non-structural (NS) regions, such as NS3, NS4B, and NS5 such that at least a portion of each amplification product contains nucleic acid sequence corresponding to the target. The one or more amplification products are produced provided that one or more nucleic acid is present in the sample, thus the presence of the one or more amplification products is indicative of the presence of Zika virus in the sample. The amplification product should contain the nucleic acid sequences that are complementary to one or more detectable probes for Zika virus. "Zika virus probe(s)" as used herein refer to oligonucleotide probes that specifically anneal to nucleic acid sequences found in the Zika virus genome. Each cycling step includes an amplification step, a hybridization step, and a detection step, in which the sample is contacted with the one or more detectable Zika virus probes for detection of the presence or absence of Zika virus in the sample.

As used herein, the term "amplifying" refers to the process of synthesizing nucleic acid molecules that are complementary to one or both strands of a template nucleic acid molecule (e.g., nucleic acid molecules from the Zika virus genome). Amplifying a nucleic acid molecule typically includes denaturing the template nucleic acid, annealing primers to the template nucleic acid at a temperature that is below the melting temperatures of the primers, and enzymatically elongating from the primers to generate an amplification product. Amplification typically requires the presence of deoxyribonucleoside triphosphates, a DNA polymerase enzyme (e.g., Platinum® Taq) and an appropriate buffer and/or co-factors for optimal activity of the polymerase enzyme (e.g., $MgCl_2$ and/or KCl).

The term "primer" as used herein is known to those skilled in the art and refers to oligomeric compounds, primarily to oligonucleotides but also to modified oligonucleotides that are able to "prime" DNA synthesis by a template-dependent DNA polymerase, i.e., the 3'-end of the, e.g., oligonucleotide provides a free 3'-OH group where further "nucleotides" may be attached by a template-dependent DNA polymerase establishing 3' to 5' phosphodiester linkage whereby deoxynucleoside triphosphates are used and whereby pyrophosphate is released.

The term "hybridizing" refers to the annealing of one or more probes to an amplification product. "Hybridization conditions" typically include a temperature that is below the melting temperature of the probes but that avoids non-specific hybridization of the probes.

The term "5' to 3' nuclease activity" refers to an activity of a nucleic acid polymerase, typically associated with the nucleic acid strand synthesis, whereby nucleotides are removed from the 5' end of nucleic acid strand.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacteus, T. rubens, Bacillus stearothermophilus*, and *Methanothermus fervidus*. Nonetheless, polymerases that are not thermostable also can be employed in PCR assays provided the enzyme is replenished, if necessary.

The term "complement thereof" refers to nucleic acid that is both the same length as, and exactly complementary to, a given nucleic acid.

The term "extension" or "elongation" when used with respect to nucleic acids refers to when additional nucleotides (or other analogous molecules) are incorporated into the nucleic acids. For example, a nucleic acid is optionally extended by a nucleotide incorporating biocatalyst, such as a polymerase that typically adds nucleotides at the 3' terminal end of a nucleic acid.

The terms "identical" or percent "identity" in the context of two or more nucleic acid sequences, refer to two or more sequences or subsequences that are the same or have a specified percentage of nucleotides that are the same, when compared and aligned for maximum correspondence, e.g., as measured using one of the sequence comparison algorithms available to persons of skill or by visual inspection. Exemplary algorithms that are suitable for determining percent sequence identity and sequence similarity are the BLAST programs, which are described in, e.g., Altschul et al. (1990) "Basic local alignment search tool" *J. Mol. Biol.* 215:403-410, Gish et al. (1993) "Identification of protein coding regions by database similarity search" *Nature Genet.* 3:266-272, Madden et al. (1996) "Applications of network BLAST server" Meth. Enzymol. 266:131-141, Altschul et al. (1997) "Gapped BLAST and PSI-BLAST: a new generation of protein database search programs" *Nucleic Acids Res.* 25:3389-3402, and Zhang et al. (1997) "PowerBLAST: A new network BLAST application for interactive or automated sequence analysis and annotation" Genome Res. 7:649-656, which are each incorporated herein by reference.

A "modified nucleotide" in the context of an oligonucleotide refers to an alteration in which at least one nucleotide of the oligonucleotide sequence is replaced by a different nucleotide that provides a desired property to the oligonucleotide. Exemplary modified nucleotides that can be substituted in the oligonucleotides described herein include, e.g., a t-butyl benzyl, a C5-methyl-dC, a C5-ethyl-dC, a C5-methyl-dU, a C5-ethyl-dU, a 2,6-diaminopurine, a C5-propynyl-dC, a C5-propynyl-dU, a C7-propynyl-dA, a C7-propynyl-dG, a C5-propargylamino-dC, a C5-propargylamino-dU, a C7-propargylamino-dA, a C7-propargylamino-dG, a 7-deaza-2-deoxyxanthosine, a pyrazolopyrimidine analog, a pseudo-dU, a nitro pyrrole, a nitro indole, 2'-0-methyl ribo-U, 2'-0-methyl ribo-C, an N4-ethyl-dC, an N6-methyl-dA, and the like. Many other modified nucleotides that can be substituted in the oligonucleotides are referred to herein or are otherwise known in the art. In certain embodiments, modified nucleotide substitutions modify melting temperatures (Tm) of the oligonucleotides relative to the melting temperatures of corresponding unmodified oligonucleotides. To further illustrate, certain modified nucleotide substitutions can reduce non-specific nucleic acid amplification (e.g., minimize primer dimer formation or the like), increase the yield of an intended target amplicon, and/or the like in some embodiments. Examples of these types of nucleic acid modifications are described in, e.g., U.S. Pat. No. 6,001,611, which is incorporated herein by reference. Other modified nucleotide substitutions may alter the stability of the oligonucleotide, or provide other desirable features.

Detection of Zika Virus

The present disclosure provides methods to detect Zika virus by amplifying, for example, a portion of the Zika virus nucleic acid sequence. Nucleic acid sequences of Zika virus are available (e.g., Reference Strain: Uganda 1957, Accession: NC_012532). Specifically, primers and probes to amplify and detect Zika virus nucleic acid molecule targets are provided by the embodiments in the present disclosure.

For detection of Zika virus, primers and probes to amplify the Zika virus are provided. Zika virus nucleic acids other than those exemplified herein can also be used to detect Zika virus in a sample. For example, functional variants can be evaluated for specificity and/or sensitivity by those of skill in the art using routine methods. Representative functional variants can include, e.g., one or more deletions, insertions, and/or substitutions in the Zika virus nucleic acids disclosed herein.

More specifically, embodiments of the oligonucleotides each include a nucleic acid with a sequence selected from SEQ ID NOs:1-12, a substantially identical variant thereof in which the variant has at least, e.g., 80%, 90%, or 95% sequence identity to one of SEQ ID NOs:1-12, or a complement of SEQ ID NOs:1-12 and the variant.

TABLE 1

Zika Virus Forward Primers
Forward Primers

| Oligo Name | SEQ ID NO: | Sequence | Modifications |
|---|---|---|---|
| ZIKF1151_21TBB | 1 | AACATGGCGGAGGTAAGATCJ | J = t-butylbenzyl dC |
| ZIKF9806_20TBB | 2 | CTCCCACCACTTCAACAAGJ | J = t-butylbenzyl dC |
| ZIKF6006_21TBB | 3 | GAACCCCAACAAACCTGGAGJ | J = t-butylbenzyl dA |
| ZIKF7369_26TBB | 4 | TTGTGGATGGAATAGTGGTAACTGAJ | J = t-butylbenzyl dC |

TABLE 2

Zika Virus Reverse Primers
Reverse Primers

| Oligo Name | SEQ ID NO: | Sequence | Modifications |
|---|---|---|---|
| ZIKR1236_30TBB | 5 | TAATGTTCTTTTGCAGACATATTGAGTGTJ | J = t-butylbenzyl dC |
| ZIKR9896_19_TBB | 6 | CAGTCTCCCGGATGCTCCJ | J = t-butylbenzyl dA |
| ZIKR6075_26TBB | 7 | CTGGAGGTAAATGTTGTCAAGAAGCJ | J = t-butylbenzyl dA |
| ZIKR7470_17_TBB | 8 | CJAGCCTCCCCCCATCC | J = tbutylbenzyl dC |

TABLE 3

Zika Virus Probes
Probes

| Oligo Name | SEQ ID NO: | Sequence | Modifications |
|---|---|---|---|
| ZIKPS1197_35HQ8 | 9 | HTGCCCAACQACAAGGTGAAGCCTACCTTGACAAGCAP | P = phosphate, H = HEX-Thr, Q = BHQ2 |
| ZIKPS9844_27HQ8 | 10 | HCCGCCACCQAAGATGAACTGATTGGCCGP | P = phosphate, H = HEX-Thr, Q = BHQ2 |
| ZIKPS6019_33HQ8 | 11 | HTGGAGGTGQGGTGTGCAGAGACTGATGAAGACCAP | P = phosphate, H = HEX-Thr, Q = BHQ2 |
| ZIKPS7372_42HQ8 | 12 | HTGACACAAQTGACAATTGACCCCCAAGTGGAGAAGAAGATGGGP | P = phosphate, H = HEX-Thr, Q = BHQ2 |

In one embodiment, the above described sets of Zika virus primers and probes are used in order to provide for detection of Zika virus in a biological sample suspected of containing Zika virus (Tables 1-3). The sets of primers and probes may comprise or consist of the primers and probes specific for the Zika virus nucleic acid sequences, comprising or consisting of the nucleic acid sequences of SEQ ID NOs:1-12. In another embodiment, the primers and probes for the Zika virus target comprise or consist of a functionally active variant of any of the primers and probes of SEQ ID NOs:1-12.

A functionally active variant of any of the primers and/or probes of SEQ ID NOs:1-12 may be identified by using the primers and/or probes in the disclosed methods. A functionally active variant of a primer and/or probe of any of the SEQ ID NOs:1-12 pertains to a primer and/or probe which provide a similar or higher specificity and sensitivity in the described method or kit as compared to the respective sequence of SEQ ID NOs:1-12.

The variant may, e.g., vary from the sequence of SEQ ID NOs:1-12 by one or more nucleotide additions, deletions or substitutions such as one or more nucleotide additions, deletions or substitutions at the 5' end and/or the 3' end of the respective sequence of SEQ ID NOs:1-12. As detailed above, a primer (and/or probe) may be chemically modified, i.e., a primer and/or probe may comprise a modified nucleotide or a non-nucleotide compound. A probe (or a primer) is then a modified oligonucleotide. "Modified nucleotides" (or "nucleotide analogs") differ from a natural "nucleotide" by some modification but still consist of a base or base-like compound, a pentofuranosyl sugar or a pentofuranosyl sugar-like compound, a phosphate portion or phosphate-like portion, or combinations thereof. For example, a "label" may be attached to the base portion of a "nucleotide" whereby a "modified nucleotide" is obtained. A natural base in a "nucleotide" may also be replaced by, e.g., a 7-desazapurine whereby a "modified nucleotide" is obtained as well. The terms "modified nucleotide" or "nucleotide analog" are used interchangeably in the present application. A "modified nucleoside" (or "nucleoside analog") differs from a natural nucleoside by some modification in the manner as outlined above for a "modified nucleotide" (or a "nucleotide analog").

Oligonucleotides including modified oligonucleotides and oligonucleotide analogs that amplify a nucleic acid molecule encoding the Zika virus target, e.g., nucleic acids encoding alternative portions of Zika virus can be designed using, for example, a computer program such as OLIGO (Molecular Biology Insights Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 8 to 50 nucleotides in length (e.g., 8, 10, 12, 14, 16, 18, 20, 22, 24, 26, 28, 30, 32, 34, 36, 38, 40, 42, 44, 46, 48, or 50 nucleotides in length).

In addition to a set of primers, the methods may use one or more probes in order to detect the presence or absence of Zika virus. The term "probe" refers to synthetically or biologically produced nucleic acids (DNA or RNA), which by design or selection, contain specific nucleotide sequences that allow them to hybridize under defined predetermined stringencies specifically (i.e., preferentially) to "target nucleic acids", in the present case to a Zika virus (target) nucleic acid. A "probe" can be referred to as a "detection probe" meaning that it detects the target nucleic acid.

In some embodiments, the described Zika virus probes can be labeled with at least one fluorescent label. In one embodiment, the Zika virus probes can be labeled with a donor fluorescent moiety, e.g., a fluorescent dye, and a corresponding acceptor moiety, e.g., a quencher.

In one embodiment, the probe comprises or consists of a fluorescent moiety and the nucleic acid sequences comprise or consist of SEQ ID NOs:9-12.

Designing oligonucleotides to be used as probes can be performed in a manner similar to the design of primers. Embodiments may use a single probe or a pair of probes for detection of the amplification product. Depending on the embodiment, the probe(s) use may comprise at least one label and/or at least one quencher moiety. As with the primers, the probes usually have similar melting temperatures, and the length of each probe must be sufficient for sequence-specific hybridization to occur but not so long that fidelity is reduced during synthesis. Oligonucleotide probes are generally 15 to 40 (e.g., 16, 18, 20, 21, 22, 23, 24, or 25) nucleotides in length.

Constructs can include vectors each containing one of Zika virus primers and probes nucleic acid molecules (e.g., SEQ ID NOs: 1, 2, 3, 4, 5, 6, 7, 8, 9, and 10). Constructs can be used, for example, as control template nucleic acid molecules. Vectors suitable for use are commercially available and/or produced by recombinant nucleic acid technology methods routine in the art. Zika virus nucleic acid molecules can be obtained, for example, by chemical synthesis, direct cloning from Zika virus, or by nucleic acid amplification.

Constructs suitable for use in the methods typically include, in addition to the Zika virus nucleic acid molecules (e.g., a nucleic acid molecule that contains one or more sequences of SEQ ID NOs:1-12), sequences encoding a selectable marker (e.g., an antibiotic resistance gene) for selecting desired constructs and/or transformants, and an origin of replication. The choice of vector systems usually depends upon several factors, including, but not limited to, the choice of host cells, replication efficiency, selectability, inducibility, and the ease of recovery.

Constructs containing Zika virus nucleic acid molecules can be propagated in a host cell. As used herein, the term host cell is meant to include prokaryotes and eukaryotes such as yeast, plant and animal cells. Prokaryotic hosts may include *E. coli, Salmonella typhimurium, Serratia marcescens*, and *Bacillus subtilis*. Eukaryotic hosts include yeasts such as *S. cerevisiae, S. pombe, Pichia pastoris*, mammalian cells such as COS cells or Chinese hamster ovary (CHO) cells, insect cells, and plant cells such as *Arabidopsis thaliana* and *Nicotiana tabacum*. A construct can be introduced into a host cell using any of the techniques commonly known to those of ordinary skill in the art. For example, calcium phosphate precipitation, electroporation, heat shock, lipofection, microinjection, and viral-mediated nucleic acid transfer are common methods for introducing nucleic acids into host cells. In addition, naked DNA can be delivered directly to cells (see, e.g., U.S. Pat. Nos. 5,580,859 and 5,589,466).

Polymerase Chain Reaction (PCR)

U.S. Pat. Nos. 4,683,202, 4,683,195, 4,800,159, and 4,965,188 disclose conventional PCR techniques. PCR typically employs two oligonucleotide primers that bind to a selected nucleic acid template (e.g., DNA or RNA). Primers useful in some embodiments include oligonucleotides capable of acting as points of initiation of nucleic acid synthesis within the described Zika virus nucleic acid sequences (e.g., SEQ ID NOs: 1-8). A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min (e.g., 1 min to 2 min 30 sec, or 1.5 min).

If the double-stranded template nucleic acid is denatured by heat, the reaction mixture is allowed to cool to a temperature that promotes annealing of each primer to its target sequence. The temperature for annealing is usually from about 35° C. to about 65° C. (e.g., about 40° C. to about 60° C.; about 45° C. to about 50° C.). Annealing times can be from about 10 sec to about 1 min (e.g., about 20 sec to about 50 sec; about 30 sec to about 40 sec). The reaction mixture is then adjusted to a temperature at which the activity of the polymerase is promoted or optimized, i.e., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template (e.g., the temperature for extension generally ranges from about 40° C. to about 80° C. (e.g., about 50° C. to about 70° C.; about 60° C.). Extension times can be from about 10 sec to about 5 min (e.g., about 30 sec to about 4 min; about 1 min to about 3 min; about 1 min 30 sec to about 2 min).

The genome of a retrovirus or RNA virus, such as Zika virus as well as other flaviviruses, is comprised of a ribonucleic acid, i.e., RNA. In such case, the template nucleic acid, RNA, must first be transcribed into complementary DNA (cDNA) via the action of the enzyme reverse transcriptase. Reverse transcriptases use an RNA template and a short primer complementary to the 3' end of the RNA to direct synthesis of the first strand cDNA, which can then be used directly as a template for polymerase chain reaction.

PCR assays can employ Zika virus nucleic acid such as RNA or DNA (cDNA). The template nucleic acid need not be purified; it may be a minor fraction of a complex mixture, such as Zika virus nucleic acid contained in human cells. Zika virus nucleic acid molecules may be extracted from a biological sample by routine techniques such as those described in Diagnostic Molecular Microbiology: Principles and Applications (Persing et al. (eds), 1993, American Society for Microbiology, Washington D.C.). Nucleic acids can be obtained from any number of sources, such as plasmids, or natural sources including bacteria, yeast, viruses, organelles, or higher organisms such as plants or animals.

The oligonudeotide primers (e.g., SEQ ID NOs:1-8) are combined with PCR reagents under reaction conditions that induce primer extension. For example, chain extension reactions generally include 50 mM KCl, 10 mM Tris-HCl (pH 8.3), 15 mM $MgCl_2$, 0.001% (w/v) gelatin, 0.5-1.0 lag denatured template DNA, 50 pmoles of each oligonudeotide primer, 2.5 U of Taq polymerase, and 10% DMSO). The reactions usually contain 150 to 320 μM each of dATP, dCTP, dTTP, dGTP, or one or more analogs thereof.

The newly-synthesized strands form a double-stranded molecule that can be used in the succeeding steps of the reaction. The steps of strand separation, annealing, and elongation can be repeated as often as needed to produce the desired quantity of amplification products corresponding to the target Zika virus nucleic acid molecules. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Fluorescence Resonance Energy Transfer (FRET)

FRET technology (see, for example, U.S. Pat. Nos. 4,996,143, 5,565,322, 5,849,489, and 6,162,603) is based on a concept that when a donor fluorescent moiety and a corresponding acceptor fluorescent moiety are positioned within a certain distance of each other, energy transfer takes place between the two fluorescent moieties that can be visualized or otherwise detected and/or quantitated. The donor typically transfers the energy to the acceptor when the donor is excited by light radiation with a suitable wavelength. The acceptor typically re-emits the transferred energy in the form of light radiation with a different wavelength. In certain systems, non-fluorescent energy can be transferred between donor and acceptor moieties, by way of biomolecules that include substantially non-fluorescent donor moieties (see, for example, U.S. Pat. No. 7,741,467).

In one example, an oligonucleotide probe can contain a donor fluorescent moiety (e.g., HEX) and a corresponding quencher (e.g., BlackHole Quenchers™ (BHQ)), which may or not be fluorescent, and which dissipates the transferred energy in a form other than light. When the probe is intact, energy transfer typically occurs between the donor and acceptor moieties such that fluorescent emission from the donor fluorescent moiety is quenched the acceptor moiety. During an extension step of a polymerase chain reaction, a probe bound to an amplification product is cleaved by the 5' to 3' nuclease activity of, e.g., a Taq Polymerase such that the fluorescent emission of the donor fluorescent moiety is no longer quenched. Exemplary probes for this purpose are described in, e.g., U.S. Pat. Nos. 5,210,015, 5,994,056, and 6,171,785. Commonly used donor-acceptor pairs include the FAM-TAMRA pair. Commonly used quenchers are DABCYL and TAMRA. Commonly used dark quenchers include BlackHole Quenchers™ (BHQ), (Biosearch Technologies, Inc., Novato, Cal.), Iowa Black™, (Integrated DNA Tech., Inc., Coralville, Iowa), BlackBerry™ Quencher 650 (BBQ-650), (Berry & Assoc., Dexter, Mich.).

In another example, two oligonucleotide probes, each containing a fluorescent moiety, can hybridize to an amplification product at particular positions determined by the complementarity of the oligonucleotide probes to the Zika virus target nucleic acid sequence. Upon hybridization of the oligonucleotide probes to the amplification product nucleic acid at the appropriate positions, a FRET signal is generated. Hybridization temperatures can range from about 35° C. to about 65° C. for about 10 sec to about 1 min.

Fluorescent analysis can be carried out using, for example, a photon counting epifluorescent microscope system (containing the appropriate dichroic mirror and filters for monitoring fluorescent emission at the particular range), a photon counting photomultiplier system, or a fluorimeter. Excitation to initiate energy transfer, or to allow direct detection of a fluorophore, can be carried out with an argon ion laser, a high intensity mercury (Hg) arc lamp, a xenon lamp, a fiber optic light source, or other high intensity light source appropriately filtered for excitation in the desired range.

As used herein with respect to donor and corresponding acceptor moieties "corresponding" refers to an acceptor fluorescent moiety or a dark quencher having an absorbance spectrum that overlaps the emission spectrum of the donor fluorescent moiety. The wavelength maximum of the emission spectrum of the acceptor fluorescent moiety should be at least 100 nm greater than the wavelength maximum of the excitation spectrum of the donor fluorescent moiety. Accordingly, efficient non-radiative energy transfer can be produced therebetween.

Fluorescent donor and corresponding acceptor moieties are generally chosen for (a) high efficiency Foerster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, helium-cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC Red 640, LC Red 705, Cy5, Cy5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate, or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

The donor and acceptor fluorescent moieties can be attached to the appropriate probe oligonucleotide via a linker arm. The length of each linker arm is important, as the linker arms will affect the distance between the donor and acceptor fluorescent moieties. The length of a linker arm can be the distance in Angstroms (Å) from the nucleotide base to the fluorescent moiety. In general, a linker arm is from about 10 Å to about 25 Å. The linker arm may be of the kind described in WO 84/03285. WO 84/03285 also discloses methods for attaching linker arms to a particular nucleotide base, and also for attaching fluorescent moieties to a linker arm.

An acceptor fluorescent moiety, such as an LC Red 640, can be combined with an oligonucleotide that contains an amino linker (e.g., C6-amino phosphoramidites available from ABI (Foster City, Calif.) or Glen Research (Sterling, Va.)) to produce, for example, LC Red 640-labeled oligonucleotide. Frequently used linkers to couple a donor fluorescent moiety such as fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, such as CX-fluorescein-CPG from BioGenex (San Ramon, Calif.)), or 3'-amino-CPGs that require coupling of a fluorescein-NHS-ester after oligonucleotide synthesis.

Detection of Zika Virus

The present disclosure provides methods for detecting the presence or absence of Zika virus in a biological or non-biological sample. Methods provided avoid problems of sample contamination, false negatives, and false positives. The methods include performing at least one cycling step that includes amplifying a portion of Zika virus target nucleic acid molecules from a sample using one or more pairs of Zika virus primers, and a FRET detecting step. Multiple cycling steps are performed, preferably in a thermocycler. Methods can be performed using the Zika virus primers and probes to detect the presence of Zika virus, and the detection of Zika virus indicates the presence of Zika virus in the sample.

As described herein, amplification products can be detected using labeled hybridization probes that take advantage of FRET technology. One FRET format utilizes TaqMan® technology to detect the presence or absence of an amplification product, and hence, the presence or absence of Zika virus. TaqMan® technology utilizes one single-stranded hybridization probe labeled with, e.g., one fluorescent dye (e.g., HEX) and one quencher (e.g., BHQ), which may or may not be fluorescent. When a first fluorescent moiety is excited with light of a suitable wavelength, the absorbed energy is transferred to a second fluorescent moiety or a dark quencher according to the principles of FRET. The second moiety is generally a quencher molecule. During the annealing step of the PCR reaction, the labeled hybridization probe binds to the target DNA (i.e., the amplification product) and is degraded by the 5' to 3' nuclease activity of, e.g., the Taq Polymerase during the subsequent elongation phase. As a result, the fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems) uses TaqMan® technology, and is suitable for performing the methods described herein for detecting the presence or absence of Zika virus in the sample.

Molecular beacons in conjunction with FRET can also be used to detect the presence of an amplification product using the real-time PCR methods. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., amplification products), the secondary structure of the probe is disrupted and the fluorescent moieties become separated from one another such that after excitation with light of a suitable wavelength, the emission of the first fluorescent moiety can be detected.

Another common format of FRET technology utilizes two hybridization probes. Each probe can be labeled with a different fluorescent moiety and are generally designed to hybridize in close proximity to each other in a target DNA molecule (e.g., an amplification product). A donor fluorescent moiety, for example, fluorescein, is excited at 470 nm by the light source of the LightCycler® Instrument. During FRET, the fluorescein transfers its energy to an acceptor fluorescent moiety such as LightCycler®-Red 640 (LC Red 640) or LightCycler®-Red 705 (LC Red 705). The acceptor fluorescent moiety then emits light of a longer wavelength, which is detected by the optical detection system of the LightCycler® instrument. Efficient FRET can only take place when the fluorescent moieties are in direct local proximity and when the emission spectrum of the donor fluorescent moiety overlaps with the absorption spectrum of the acceptor fluorescent moiety. The intensity of the emitted signal can be correlated with the number of original target DNA molecules (e.g., the number of Zika virus genomes). If amplification of Zika virus target nucleic acid occurs and an amplification product is produced, the step of hybridizing results in a detectable signal based upon FRET between the members of the pair of probes.

Generally, the presence of FRET indicates the presence of Zika virus in the sample, and the absence of FRET indicates the absence of Zika virus in the sample. Inadequate specimen collection, transportation delays, inappropriate transportation conditions, or use of certain collection swabs (calcium alginate or aluminum shaft) are all conditions that can affect the success and/or accuracy of a test result, however.

Representative biological samples that can be used in practicing the methods include, but are not limited to respiratory specimens, urine, fecal specimens, blood specimens, plasma, dermal swabs, nasal swabs, wound swabs, blood cultures, skin, and soft tissue infections. Collection and storage methods of biological samples are known to those of skill in the art. Biological samples can be processed (e.g., by nucleic acid extraction methods and/or kits known in the art) to release Zika virus nucleic acid or in some cases, the biological sample can be contacted directly with the PCR reaction components and the appropriate oligonucleotides.

Melting curve analysis is an additional step that can be included in a cycling profile. Melting curve analysis is based on the fact that DNA melts at a characteristic temperature called the melting temperature (Tm), which is defined as the temperature at which half of the DNA duplexes have separated into single strands. The melting temperature of a DNA depends primarily upon its nucleotide composition. Thus, DNA molecules rich in G and C nucleotides have a higher Tm than those having an abundance of A and T nucleotides. By detecting the temperature at which signal is lost, the melting temperature of probes can be determined. Similarly, by detecting the temperature at which signal is generated, the annealing temperature of probes can be determined. The melting temperature(s) of the Zika virus probes from the Zika virus amplification products can confirm the presence or absence of Zika virus in the sample.

Within each thermocycler run, control samples can be cycled as well. Positive control samples can amplify target nucleic acid control template (other than described amplification products of target genes) using, for example, control primers and control probes. Positive control samples can also amplify, for example, a plasmid construct containing the target nucleic acid molecules. Such a plasmid control can be amplified internally (e.g., within the sample) or in a separate sample run side-by-side with the patients' samples using the same primers and probe as used for detection of the intended target. Such controls are indicators of the success or failure of the amplification, hybridization, and/or FRET reaction. Each thermocycler run can also include a negative control that, for example, lacks target template DNA. Negative control can measure contamination. This ensures that the system and reagents would not give rise to a false positive signal. Therefore, control reactions can readily determine, for example, the ability of primers to anneal with sequence-specificity and to initiate elongation, as well as the ability of probes to hybridize with sequence-specificity and for FRET to occur.

In an embodiment, the methods include steps to avoid contamination. For example, an enzymatic method utilizing uracil-DNA glycosylase is described in U.S. Pat. Nos. 5,035,996, 5,683,896 and 5,945,313 to reduce or eliminate contamination between one thermocycler run and the next.

Conventional PCR methods in conjunction with FRET technology can be used to practice the methods. In one embodiment, a LightCycler® instrument is used. The following patent applications describe real-time PCR as used in the LightCycler® technology: WO 97/46707, WO 97/46714, and WO 97/46712.

The LightCycler® can be operated using a PC workstation and can utilize a Windows NT operating system. Signals from the samples are obtained as the machine positions the capillaries sequentially over the optical unit. The software can display the fluorescence signals in real-time immediately after each measurement. Fluorescent acquisition time is 10-100 milliseconds (msec). After each cycling step, a quantitative display of fluorescence vs. cycle number can be continually updated for all samples. The data generated can be stored for further analysis.

As an alternative to FRET, an amplification product can be detected using a double-stranded DNA binding dye such as a fluorescent DNA binding dye (e.g., SYBR® Green or SYBR® Gold (Molecular Probes)). Upon interaction with the double-stranded nucleic acid, such fluorescent DNA binding dyes emit a fluorescence signal after excitation with light at a suitable wavelength. A double-stranded DNA binding dye such as a nucleic acid intercalating dye also can be used. When double-stranded DNA binding dyes are used, a melting curve analysis is usually performed for confirmation of the presence of the amplification product.

One of skill in the art would appreciate that other nucleic acid- or signal-amplification methods may also be employed. Examples of such methods include, without limitation, branched DNA signal amplification, loop-mediated isothermal amplification (LAMP), nucleic acid sequence-based amplification (NASBA), self-sustained sequence replication (3SR), strand displacement amplification (SDA), or smart amplification process version 2 (SMAP 2).

It is understood that the embodiments of the present disclosure are not limited by the configuration of one or more commercially available instruments.

Articles of Manufacture/Kits

Embodiments of the present disclosure further provide for articles of manufacture or kits to detect Zika virus. An article of manufacture can include primers and probes used to detect the Zika virus gene target, together with suitable packaging materials. Representative primers and probes for detection of Zika virus are capable of hybridizing to Zika virus target nucleic acid molecules. In addition, the kits may also include suitably packaged reagents and materials needed for DNA immobilization, hybridization, and detection, such solid supports, buffers, enzymes, and DNA standards. Methods of designing primers and probes are disclosed herein, and representative examples of primers and probes that amplify and hybridize to Zika virus target nucleic acid molecules are provided.

Articles of manufacture can also include one or more fluorescent moieties for labeling the probes or, alternatively, the probes supplied with the kit can be labeled. For example, an article of manufacture may include a donor and/or an acceptor fluorescent moiety for labeling the Zika virus probes. Examples of suitable FRET donor fluorescent moieties and corresponding acceptor fluorescent moieties are provided above.

Articles of manufacture can also contain a package insert or package label having instructions thereon for using the Zika virus primers and probes to detect Zika virus in a sample. Articles of manufacture may additionally include reagents for carrying out the methods disclosed herein (e.g., buffers, polymerase enzymes, co-factors, or agents to prevent contamination). Such reagents may be specific for one of the commercially available instruments described herein.

Embodiments of the present disclosure will be further described in the following examples, which do not limit the scope of the invention described in the claims.

EXAMPLES

The following examples and figures are provided to aid the understanding of the subject matter, the true scope of which is set forth in the appended claims. It is understood that modifications can be made in the procedures set forth without departing from the spirit of the invention.

The targeted region of the Zika virus genome included both structural regions (e.g., Envelope (E)) as well as non-structural regions (e.g., NS3, NS4B, and NS5). All nucleic acid sequences were aligned and all primers and probes were considered and scored for their predicted inclusivity for all known Zika isolates and other properties. Positive controls were created by considering the sequences of viruses in circulation. Sequences from publicly available databases were exported and sequence alignments were performed. The sequences were then filtered to consider contemporary sequences from 2007 on onward. A cDNA done was fabricated to serve as a positive DNA or RNA control. The cDNA done was based on the Suriname 2015 strain relative to the reference strain (African lineage, Uganda), and a historical African strain. The sequences were aligned relative to the primers and probes and slight adjustments were made to the sequences.

Example 1: Detection of Cultured Zika Virus

Figure 2:
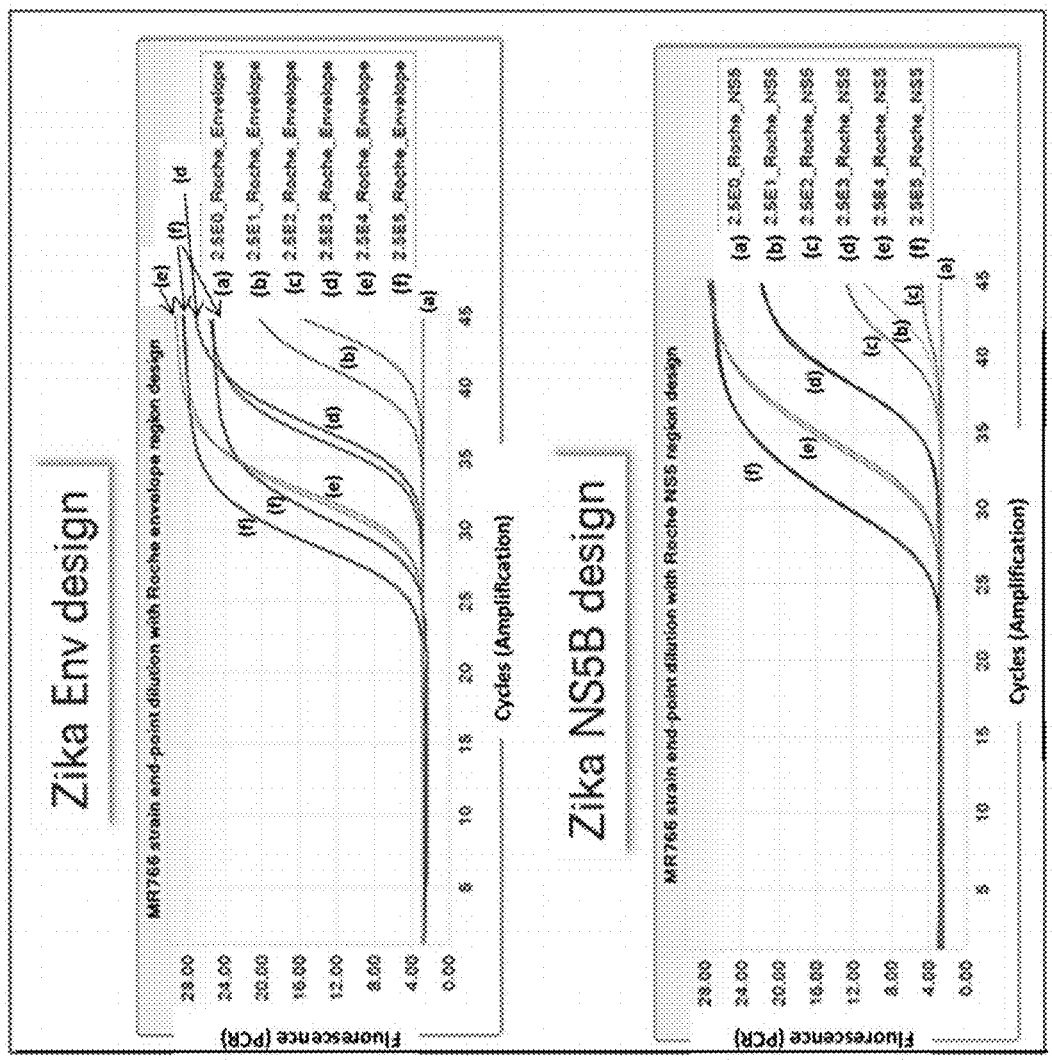
FIG. 2 shows PCR growth curves of experiments showing that the primers and probes specific for the E and NS5 regions of the Zika virus genome detect Zika virus.
Figure 3:
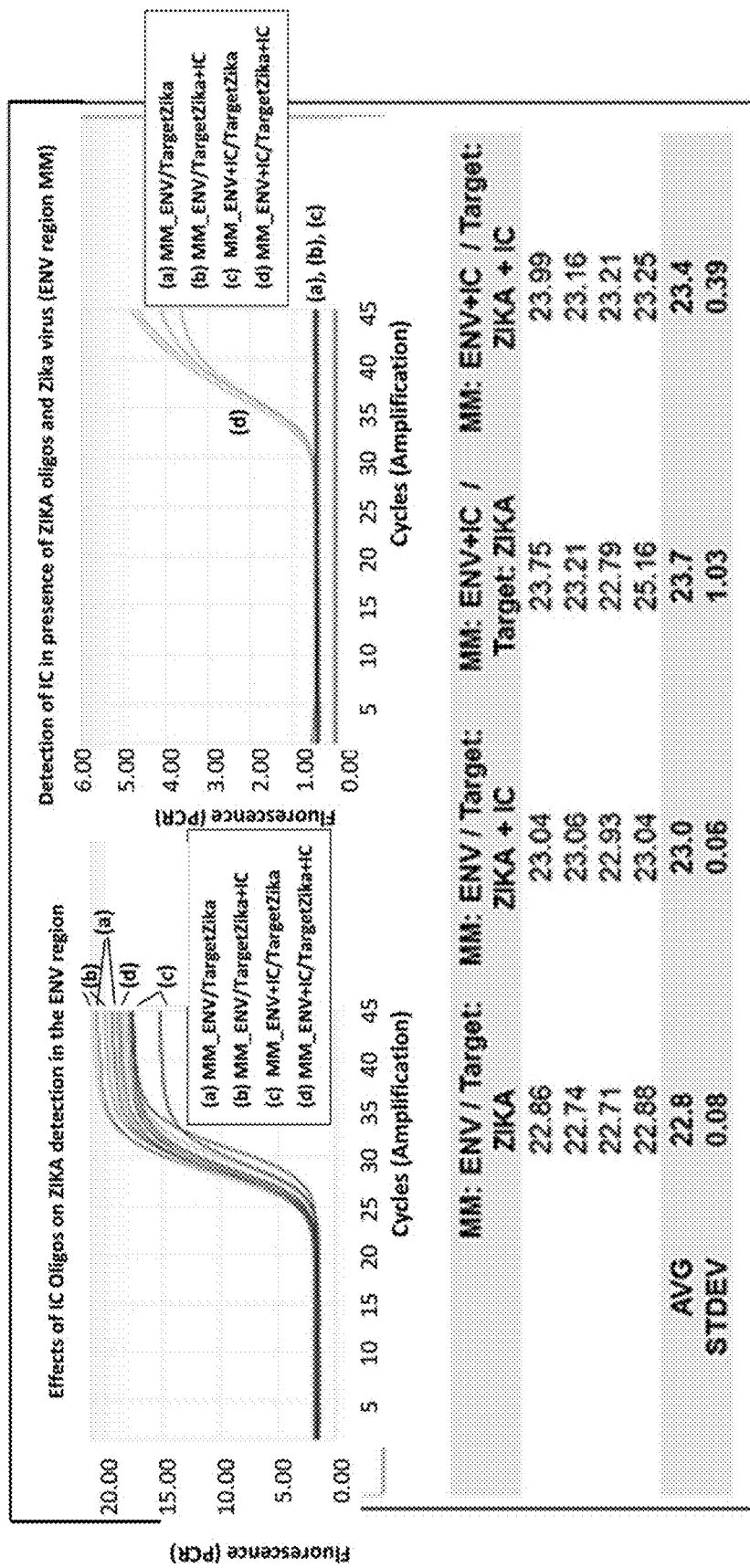
FIG. 3 shows PCR growth curves of experiments, in the presence of an internal reference control, showing the capacity of the Zika virus primers and probes for multiplexing with other targets/nucleic acids.

RNA from cultured MR 766 Zika virus was extracted using QIAmp Viral RNA Mini Kit (Qiagen). Total RNA was quantitated using RiboGreen Assay (ThermoFisher Scientific), Qubit (ThermoFisher Scientific), and NanoDrop (ThermoFisher Scientific). Quantitative real-time RT-PCR was run using primers and probes targeting the E, NS3, and NS5 regions at varying concentrations of Zika RNA (i.e., $2.5 \times 10^4$ and $2.5 \times 10^6$ copies of RNA/ml). Results show that the primers and probes are able to detect the E regions (SEQ ID NOs:1, 5, and 9), NS3 (SEQ ID NOs:3, 7, and 11), and NS5 (SEQ ID NOs:2, 6, and 10) (see FIG. 1). Further studies were conducted on a wider range of Zika RNA starting concentrations (from $2.5 \times 10^0$, $2.5 \times 10^1$, $2.5 \times 10^2$, $2.5 \times 10^3$, $2.5 \times 10^4$, and $2.5 \times 10^5$ copies of RNA/ml), showing that primers and probes were able to detect the E and NS5 regions of Zika virus in a dose-dependent fashion (see FIG. 2). Additional assays targeting the E region, in the presence of an internal reference control set of primers/probes, demonstrate the capacity of the Zika virus primers and probes to detect Zika virus and to be multiplexed with other assays for detection (see FIG. 3).

Example 2: Detection of Zika Virus in Biological Samples

Figure 4:
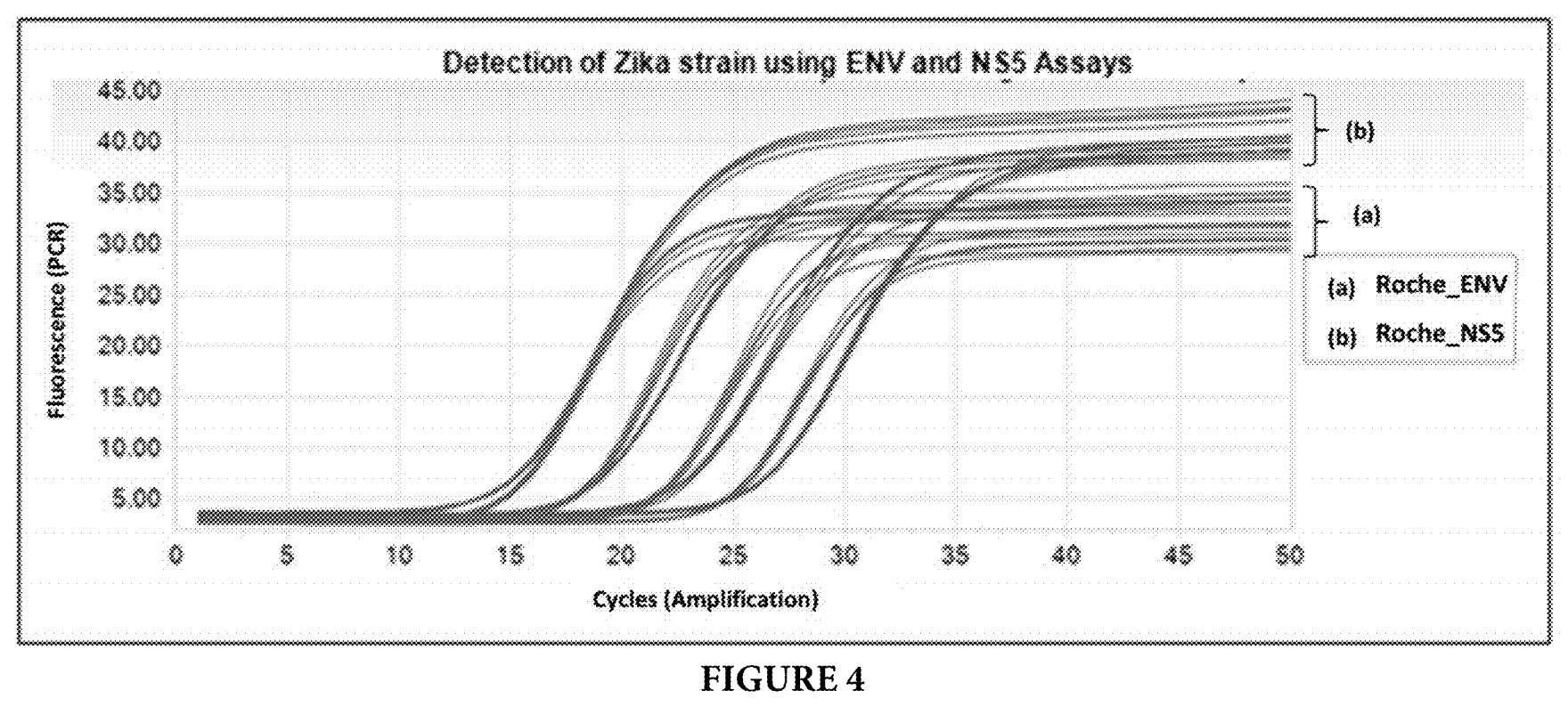

In order to show that the primers and probes detecting Zika virus were able to detect Zika virus from biological samples, e.g., bodily fluids, the primers and probes targeting the E and NS5 regions of the Zika virus genome were tested against Zika virus RNA obtained from plasma samples. Results show that the Zika virus primers and probes were able to detect Zika virus in plasma with specificity and sensitivity. This full process was conducted several times and the Zika primers and probes were shown to reproducibly detect Zika virus (a representative example is shown in FIG. 4). These results demonstrate that the Zika virus primers and probes detect the presence of Zika virus in biological samples, e.g., plasma.

Example 3: Assay Performance of a Zika Nucleic Acid Test for Blood Screening

Human infection with the Zika virus (ZIKV) is associated with microcephaly and neurologic disease. Since most infections are asymptomatic, blood donors may unknowingly harbor infection. ZIKV nucleic acid was detected in 2.8% of blood donors during the French Polynesia outbreak in 2013-2014, and cases of transfusion-transmission have recently been reported in Brazil. The U.S. FDA issued recommendations to reduce the risk of transfusion transmitted ZIKV. In areas of active transmission, blood establishments must cease blood collections unless donations are screened with a nucleic acid test (NAT) for ZIKV or components are pathogen reduced (PR). Currently, PR is limited to platelets and plasma products.

In response to the FDA recommendations, the cobas® Zika test, a qualitative method for detection of ZIKV RNA using polymerase chain reaction (PCR), was developed for use on the cobas® 6800/8800 Systems. These systems incorporate fully-automated sample preparation, amplification and detection, and ready-to-use reagents and controls. The test is intended to detect ZIKV RNA in plasma specimens from donors of whole blood and blood components, as well as other living donors.

The cobas® Zika test was designed to detect all ZIKV lineages. Most performance studies used ZIKV culture supernatant with titer assigned in copies/mL using ZIKV RNA transcript. Studies included specificity, sensitivity, limit of detection (LoD), interfering substances, matrix equivalency, and cross-reactivity. LoD and repeatability were assessed using 190 replicates across multiple concentrations, reagent lots, and days. Clinical sensitivity was evaluated by testing 25 samples confirmed ZIKV positive using published oligonucleotide sequences (Lanciotti, Emerg Infect Dis, 2008). In addition, 5 clinical specimens were spiked into negative pooled plasma to create 250 contrived samples at various dilutions.

Drug (IND). Testing of individual blood donor (IDT) samples from Puerto Rico were then begun. Reactive index donations were retested in simulated mini-pools (MP) of 6. Reactive index donations were also tested by a reference laboratory using a modified CDC PCR ZIKV assay, estimated viral load (VL), ZIKV IgM and IgG antibodies, and plaque reduction neutralization test (PRNT) for IgM reactive samples. Donors with reactive results were invited to enroll in a follow-up study.

3,573 donations have been screened by cobas® Zika, and 13 (0.36%) tested reactive. Additional results for 9 of these donations are shown on Table 4.

TABLE 4

Summary of Testing Results on Donations Reactive with cobas ® Zika

| Sample ID | cobas ® ZIKA | | Modified CDC | | Serology | | |
|---|---|---|---|---|---|---|---|
| | IDT | Simulated MP | PCR | Mean VL | IgG | IgM | PRNT |
| 1 | R | R | Equivocal | 4.20E+02 | Negative | Negative | N/A |
| 2 | R | R | Positive | 2.70E+03 | Positive | Positive | Pending |
| 3 | R | R | Positive | 5.90E+06 | Negative | Negative | N/A |
| 4 | R | R | Positive | 7.90E+03 | Negative | Negative | N/A |
| 5 | R | R | Positive | 5.40E+04 | Negative | Negative | N/A |
| 6 | R | NR | Positive | 3.20E+02 | Inconclusive | Equivocal | N/A |
| 7 | R | R | Positive | 4.90E+05 | Negative | Negative | N/A |
| 8 | R | R | Positive | 7.10E+03 | Negative | Negative | N/A |
| 9 | R | R | Positive | 7.60E+04 | Equivocal | Negative | N/A |

R Reactive;
NR Non-Reactive;
N/A Not applicable

The 95% Probit LoD for cobas® Zika was 8.1 copies/mL, and the results were reproducible across multiple parameters. Specificity was 100% in 500 samples collected in a ZIKV non-endemic region. Neither ZIKV detectability nor specificity was impacted by potentially-interfering substances including albumin, bilirubin, hemoglobin, human DNA and triglycerides or with various anticoagulants. Human Immunodeficiency Virus (HIV), Hepatitis B Virus (HBV), Hepatitis C Virus (HCV), Chikungunya (CHIKV), Dengue Virus (DENV) serotypes 1-4, and West Nile Virus (WNV) did not cross-react. Clinical sensitivity of cobas® Zika was 100% with 25 confirmed ZIKV positive samples from 4 different countries. Reactivity was 100% with 250 contrived samples with a range of viral concentrations.

Example 4: Detection of Zika Virus in Puerto Rican Blood Donors

The U.S. FDA issued recommendations to reduce the risk of transfusion-transmitted Zika virus (ZIKV), including cessation of blood collections in areas of active ZIKV transmission, unless donations are screened with a ZIKV nucleic acid test (NAT) or are pathogen reduced (PR). Puerto Rico was required to discontinue collections, as no FDA-approved NAT test was available and PR is available only for plasma and platelet products. In response to FDA recommendations, a qualitative PCR NAT assay was developed to detect ZIKV RNA in plasma from donors of whole blood and blood components.

The cobas® Zika test for use on the cobas® 6800/8800 Systems was developed to detect all ZIKV lineages. Performance was established with studies including specificity, sensitivity, limit of detection (LoD), potential interfering substances, matrix equivalency, and cross reactivity. The FDA approved use of the test as an Investigational New These data show that the cobas® Zika test successfully identified ZIKV-positive donations, allowing for resumption of collections in Puerto Rico.

Example 5: Alternative Assay for Identifying Zika Nucleic Acid in Specimens

The cobas® Zika test for use on the cobas® 6800/8800 systems was developed for blood screening under Investigational New Drug (IND). To establish sensitivity of the IND test, the FDA required analysis of Zika virus (ZIKV) positive specimens. Procurement of ZIKV positive specimens was challenging due to high demand, scarcity of ZIKV confirmed specimens, and barriers to shipment of specimens from some Zika endemic countries. A second ZIKV PCR assay was developed as a tool for screening specimens with unknown status. This second ZIKV PCR assay specifically uses the cobas omni Utility Channel, which is ideal for rapid prototyping and high throughput screening. The cobas omni Utility Channel utilizes most of the reagents used for cobas® IVD tests, except the assay specific primers and probes, allowing for the flexibility to perform laboratory developed tests on the platform.

The second ZIKV PCR assay that targeted a gene locus separate from gene locus targeted by the cobas® Zika test was developed using the cobas omni Utility Channel functionality of the cobas® 6800/8800 system. This assay was used to identify "possible" ZIKV specimens by screening samples collected in Colombia and El Salvador. Specimens were originally obtained from chikungunya and dengue endemic areas and found to be negative for those viruses. For screening, due to limited volumes, specimens were diluted to at least 1:3.75 and tested singly. Broad Ct acceptance criteria were used to identify "possible" ZIKV positive specimens. Specimens identified as "possible" ZIKV by this second assay were further tested in 4 replicates using RT-PCR with published CDC oligonucleotide sequences (Lanciotti, 2008) and once by the cobas® Zika test. Specimens were considered to be confirmed for ZIKV if consistent reactivity (4/4 replicates) was observed using the CDC oligonudeotides.

Of 1,296 specimens screened by the in-house assay on the cobas omni Utility Channel, 111 were identified as "possible" ZIKV positive. Thirty-seven specimens with sufficient volume were tested using the CDC oligos and the cobas® Zika test. Three additional specimens with limited volume were diluted 1:100 and tested. Of these 40 "possible" positives, 23 specimens, including the 3 diluted specimens, were confirmed positive by the CDC oligonudeotides and all were reactive with cobas® Zika. Seventeen specimens had <4/4 reactive results with the CDC oligonucleotides; 15/17 tested positive with the cobas® Zika test. The results are shown on Table 5.

TABLE 5 cobas ® Zika detection in specimens with different levels of CDC reactivity

| Number of Individual Specimens N = 40 | Number of CDC positive replicates per specimen | ZIKV Result interpretation w/CDC oligos | Number of reactive specimens using cobas ® Zika |
|---|---|---|---|
| 23 | 4 of 4 replicates | Confirmed | 23/23 reactive |
| 4 | 3 of 4 replicates | Equivocal | 4/4 reactive |
| 1 | 2 of 4 replicates | Equivocal | 1/1 reactive |
| 7 | 1 of 4 replicates | Equivocal | 6/7 reactive |
| 5 | 0 of 4 replicates | Negative | 4/5 reactive |

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed:

1. A kit for detecting a nucleic acid sequence of Zika virus in a sample, the kit comprising:
   one or more first primers, wherein the one or more first primers consists of an oligonucleotide sequence consisting of SEQ ID NO:1;
   one or more second primers, wherein the one or more second primers consists of an oligonucleotide sequence consisting of SEQ ID NO:5; and
   one or more detectable probes, wherein the one or more detectable probes consists of: (i) an oligonucleotide sequence consisting of SEQ ID NO:9, (ii) a donor fluorescent moiety, and (iii) a corresponding acceptor moiety, and wherein the one or more detectable probes is configured to hybridize to an amplicon generated by the one or more first primers and the one or more second primers.

2. The kit of claim 1, wherein the acceptor moiety is a quencher.

3. The kit of claim 1, further comprising a primer set and one or more detectable probes for detecting a nucleic acid sequence from one or more viruses, in parallel.

4. The kit of claim 3, wherein the one or more other viruses is selected from the group consisting of dengue virus, chikungunya virus, and West Nile virus.

5. The kit of claim 1, further comprising nucleotide triphosphates, nucleic acid polymerase, and buffers necessary for the function of the nucleic acid polymerase.

6. The kit of claim 1, wherein at least one of the one or more first primers, the one or more second primers, and the one or more detectable probes comprises at least one modified nucleotide.

7. A set of primers and one or more detectable probes for the detection of Zika virus in a sample, wherein the set of primers consists of: (a) one or more first primers, wherein the one or more first primers consists of an oligonucleotide sequence consisting of SEQ ID NO:1; and (b) one or more second primers, wherein the one or more second primers consists of an oligonucleotide sequence consisting of SEQ ID NO:5; and wherein the one or more detectable probes consists of: (i) an oligonucleotide sequence consisting of SEQ ID NO:9, (ii) a donor fluorescent moiety, and (iii) a corresponding acceptor moiety.

8. The set of primers and the one or more detectable probes of claim 7, wherein the donor fluorescent moiety and the corresponding acceptor moiety are within no more than 8-20 nucleotides of each other on the one or more detectable probes.

9. The set of primers and the one or more detectable probes of claim 7, wherein the acceptor moiety is a quencher.

* * * * *

SEQUENCE LISTING

```
<160> NUMBER OF SEQ ID NOS: 12

<210> SEQ ID NO 1
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (21)..(21)
<223> OTHER INFORMATION: t-butylbenzyl dC

<400> SEQUENCE: 1
aacatggcgg aggtaagatc c                                      21

<210> SEQ ID NO 2
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (20)..(20)
<223> OTHER INFORMATION: t-butylbenzyl dC

<400> SEQUENCE: 2
ctcccaccac ttcaacaagc                                        20

<210> SEQ ID NO 3
<211> LENGTH: 21
<212> TYPE: DNA
<213> ORGANISM: Artificial Sequence
<220> FEATURE:
```

```
<223> OTHER INFORMATION: Primer
<220> FEATURE:
<221> NAME/KEY: modified_base
<222> LOCATION: (21)..(21)
<223> OTHER INFORMATION: t-butylbenzyl dA

<400> SEQUENCE: 3 gaacccccaac aaacctggag a                                              21

<210> SEQ ID NO 4
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (26)..(26)
<223> OTHER INFORMATION: t-butylbenzyl dC

<400> SEQUENCE: 4
ttgtggatgg aatagtggta actgac                                          26

<210> SEQ ID NO 5
<211> LENGTH: 30
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (30)..(30)
<223> OTHER INFORMATION: t-butylbenzyl dC

<400> SEQUENCE: 5
taatgttctt ttgcagacat attgagtgtc                                      30

<210> SEQ ID NO 6
<211> LENGTH: 19
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (19)..(19)
<223> OTHER INFORMATION: t-butylbenzyl dA

<400> SEQUENCE: 6
cagtctcccg gatgctcca                                                  19

<210> SEQ ID NO 7
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: modified_base
<222> LOCATION: (26)..(26)
<223> OTHER INFORMATION: t-butylbenzyl dA

<400> SEQUENCE: 7
ctggaggtaa atgttgtcaa gaagca                                          26

<210> SEQ ID NO 8
<211> LENGTH: 17
<212> TYPE: DNA
<213> ORGANISM: Artificial Sequence
```

```
<220> FEATURE:
<223> OTHER INFORMATION: Primer
<220> FEATURE:
<221> NAME/KEY: modified_base
<222> LOCATION: (17)..(17)
<223> OTHER INFORMATION: t-butylbenzyl dC

<400> SEQUENCE: 8
agcctccccc catcccc                                                         17

<210> SEQ ID NO 9
<211> LENGTH: 35
<212> TYPE: DNA
<213> ORGANISM: Artificial Sequence
<220> FEATURE:
<223> OTHER INFORMATION: Probe

<400> SEQUENCE: 9
tgcccaacac aaggtgaagc ctaccttgac aagca                                     35

<210> SEQ ID NO 10
<211> LENGTH: 27
<212> TYPE: DNA
<213> ORGANISM: Artificial Sequence
<220> FEATURE:
<223> OTHER INFORMATION: Probe

<400> SEQUENCE: 10
ccgccaccaa gatgaactga ttggccg                                              27

<210> SEQ ID NO 11
<211> LENGTH: 33
<212> TYPE: DNA
<213> ORGANISM: Artificial Sequence
<220> FEATURE:
<223> OTHER INFORMATION: Probe

<400> SEQUENCE: 11
tggaggtggg tgtgcagaga ctgatgaaga cca                                       33

<210> SEQ ID NO 12
<211> LENGTH: 42
<212> TYPE: DNA
<213> ORGANISM: Artificial Sequence
<220> FEATURE:
<223> OTHER INFORMATION: Probe

<400> SEQUENCE: 12
tgacacaatg acaattgacc cccaagtgga gaagaagatg gg                             42
```